(12) United States Patent
Chuah et al.

(10) Patent No.: US 7,189,387 B2
(45) Date of Patent: Mar. 13, 2007

(54) ANTIPERSPIRANT OR DEODORANT COMPOSITIONS COMPRISING ACTIVATED ALUMINIUM CHLOROHYDRATE

(75) Inventors: Beng Sim Chuah, Belangor (MY); Kevin Ronald Franklin, Wirral (GB); Gordon Charles Hough, Leeds (GB)

(73) Assignee: Unilever Home & Personal Care USA division of Conopco, Inc., Chicago, IL (US)

( * ) Notice: Subject to any disclaimer, the term of this patent is extended or adjusted under 35 U.S.C. 154(b) by 518 days.

(21) Appl. No.: 10/250,891

(22) PCT Filed: Dec. 28, 2001

(86) PCT No.: PCT/EP01/15389

§ 371 (c)(1),
(2), (4) Date: Dec. 8, 2003

(87) PCT Pub. No.: WO02/055044

PCT Pub. Date: Jul. 18, 2002

(65) Prior Publication Data

US 2004/0105829 A1  Jun. 3, 2004

(30) Foreign Application Priority Data

Jan. 9, 2001 (GB) ................................. 0100549.5

(51) Int. Cl.
*A61Q 15/00* (2006.01)
*A61K 8/00* (2006.01)
*A61K 8/02* (2006.01)
*A61K 8/04* (2006.01)

(52) U.S. Cl. ............................ 424/65; 424/68; 424/400; 424/401

(58) Field of Classification Search .................. 424/65, 424/68, 400, 401
See application file for complete search history.

(56) References Cited

U.S. PATENT DOCUMENTS

| 4,359,456 | A | 11/1982 | Gosling et al. | ............... 424/68 |
| 5,384,117 | A | 1/1995 | Vu et al. | ...................... 424/66 |
| 6,428,778 | B1 | 8/2002 | Breker et al. | ................. 424/68 |
| 6,703,005 | B2 * | 3/2004 | Allan et al. | .................... 424/65 |

FOREIGN PATENT DOCUMENTS

| EP | 191 628 | 8/1986 |
| EP | 1 057 474 | 12/2000 |
| WO | 00/71091 | 11/2000 |

* cited by examiner

Primary Examiner—Shelley A. Dodson
(74) Attorney, Agent, or Firm—Karen E. Klumas

(57) ABSTRACT

Translucent anhydrous formulations containing particulate commercially available activated aluminium chlorohydrate (AACH) have a perceptible yellowness. The yellowness of translucent anhydrous compositions containing AACH can be ameliorated or eliminated whilst retaining the improved antiperspirant efficacy of AACH by controlling its water content to the range of 9 to 18%. The appearance of yellow formulations in or on a dispensing package, prior to application to the body, can appear to be neutralised to the human eye by employing a dispenser having a complementary colour in wall contacting the formulation, to promote achromicity. The complementary colour of the wall is dark green for yellow formulations.

32 Claims, No Drawings

ANTIPERSPIRANT OR DEODORANT COMPOSITIONS COMPRISING ACTIVATED ALUMINIUM CHLOROHYDRATE

The present invention relates to antiperspirant or deodorant compositions, in particular to anhydrous compositions and especially to compositions containing an activated aluminium chlorohydrate, sometimes abbreviated to AACH. The present invention also relates to packaged compositions.

BACKGROUND AND PRIOR ART

Antiperspirant or deodorant compositions are employed on a substantial scale throughout the world in order to prevent or at least reduce the extent to which humans perspire, especially in certain areas of the body such as in the armpits or occluded areas such as on the feet and/or to control the extent to which body odours emanating particularly from such occluded areas are detectable by persons with whom the subject comes into contact. In many societies, there is a manifest desire to avoid the appearance of sweat under normal social conditions, and in particular sweat that penetrates clothing worn in close proximity to those areas and to prevent the generation of body malodours. Thus, cosmetic formulations have been developed to assist society to meet its need to control sweating and odour generated in selected body areas.

In one class of antiperspirant or deodorant formulation which is attractive to a significant fraction of consumers, an antiperspirant active is employed in the form of a particulate suspension in an anhydrous medium, normally a water-immiscible fluid. Such formulations allow activated aluminium chlorohydrate to be employed instead of standard aluminium chlorohydrate. This is beneficial because the activated material is more efficacious at controlling sweat than is the standard material, ie the user does not sweat as much in the body areas to which the formulation is applied.

Activated chlorohydrate is characterised by the presence of a significant fraction, particularly at least 20% of its aluminium in Band III species, as measured by the chromatographic method described in U.S. Pat. No. 4,359,456 (Gosling et al, assigned to Lever Brothers Company). The proportion of Band III species in an aluminium chlorohydrate antiperspirant is controlled by its method of manufacture, including in particular the reaction conditions under which polymeric aluminium chlorhydroxide species are formed and the conditions under which a solid, particulate product is formed. U.S. Pat. No. 4,359,456 describes conditions under which product can be made containing at least the minimum 20% Band III aluminium species.

The appearance of any cosmetic formulation is a factor of considerable importance to a consumer. He or she uses that appearance to judge its likely suitability for its intended purpose, sometimes using objective criteria and sometimes subjectively. Judgement is made more conveniently at various stages before or during application, the first being the appearance of the formulation in the dispenser, then possibly on the applicator surface of the dispenser and finally after application to the body. In the course of the research leading to the present invention, it was observed that certain anhydrous antiperspirant formulations containing a commercially available particulate AACH had a yellow appearance when viewed through the dispensing slits of the dispenser. This appearance is different from that of currently available antiperspirant formulations which are typically white and/or opaque. Accordingly, investigations were made to identify the source of the coloration and to find means to ameliorate or eliminate it. This problem of anhydrous formulations containing AACH exhibiting undesirable yellow colour has not been hitherto identified and accordingly no teaching has been given as to how to solve it, even in disclosures relating to the preparation of AACH for incorporation in antiperspirant formulations, possibly because it is not apparent in aerosol products in which the formulations are dispensed as a stream from metal containers.

It was found that the coloration of the anhydrous formulations containing particulate AACH was attributable to the AACH itself. There are many possible causes for a particulate material to be coloured, such as the presence of minor or impurity constituents, possibly even at trace levels. Low levels impurities are commonly encountered because commercial scale production of chemicals normally have to employ relatively impure reactants or solvents for them to be economically viable. However, the source was traced not to an impurity as such, but to the residual water content of the particulate AACH, or rather to a relative lack of water. By increasing its water content, it was found possible to reduce the discoloration of the anhydrous formulation containing the AACH.

However, the proposed solution to the problem of formulation discoloration caused by commercial AACH of increasing its water content itself poses a potential threat. High water contents cause AACH to lose its enhanced efficacy as an antiperspirant compared with standard aluminium chlorohydrate (ACH), and this has lead commercial producers of AACH to dry to low water contents to ensure the preservation of efficacy. In consequence, the problem addressed by the instant invention was not simply one of removing or eliminating the colour from anhydrous formulations containing AACH, but how to do so whilst preserving to at least a substantial extent the enhanced efficacy of AACH.

In U.S. Pat. No. 5,384,117, there is described a process for varying the refractive index of particulate aluminium chlorohydrate (ACH) by varying its water content. However, this specification provides no teaching of relevance to the present invention because it relates to ACH instead of AACH. The problem of yellow coloration with AACH clearly does not arise with ACH, otherwise the patentees would have mentioned it, since they were seeking to make clear gels. Moreover, the problem for AACH of impaired efficacy with increased water content does not arise for ACH since ACH is not an activated antiperspirant having high Band III content.

It is an object of the present invention to provide a product containing a composition of reduced colour as perceived by the human eye.

It is an object of one aspect of the present invention to obtain translucent anhydrous antiperspirant formulations containing AACH having a reduced or eliminated colour compared with formulations containing commercially available AACH whilst preserving to at least a substantial extent its antiperspirant efficacy.

It is a further object of an additional aspect of the present invention to provide a dispenser which co-operates with the formulation being dispensed therefrom to reduce or eliminate the colour of that formulation, as perceived by the eye.

SUMMARY OF THE INVENTION

According to one aspect of the present invention there is provided an anhydrous antiperspirant or deodorant composition comprising particulate AACH, and a water-immiscible carrier fluid in which the AACH is suspended characterised in that the formulation is translucent and the AACH has a water content in the range of from 9 to 18% by weight.

Herein, the compositions are considered to be translucent if they would be translucent when dispensed from a suitable dispenser, either as a result of being translucent in bulk or as a result of being dispensed through a narrow aperture.

Herein by the term translucent is meant that the formulation permits the transmission therethrough of at least a minimum percentage of light at a wavelength of 580 nM and specifically at least 0.02% through 1 cm thickness.

It has been found that although both the colour of the anhydrous, translucent, formulation containing the AACH and its efficacy varies with the water content of the AACH, there is a window within which it is possible to achieve the desired objective of formulation colour reduction combined with enhanced efficacy retention. In particular, it has been found that the colour of such a formulation containing the AACH is comparatively sensitive to changes in its water content. Herein, the level of water in the AACH is by weight, based on the total weight of the AACH particles, unless otherwise stated.

As the water content was increased from the low level in AACH commercially available in the United Kingdom in 2000, in the region of 5 to 8% by weight, it was observed first to lead to a decrease in formulation colour, but a level was reached at which a further increase in water content no longer lead to a further decrease in formulation colour, and indeed in some formulations an increase in formulation colour was observed when such a further increase in water content of the AACH was made.

On the other hand, it has been discovered that over a relatively wide range of water contents, the efficacy of the AACH, as indicated by its Band III content, remains relatively insensitive to change in water content, but that a level is reached at which the efficacy becomes progressively more sensitive to increases in water content. Furthermore, it was observed that change in the rate of impairment of efficacy with increase in water content was particularly noticeable in the region in which formulation colour ceased or increased with increase in AACH water content. The invention water level selection in AACH avoids the region containing commercially available AACH which revealed the problem of formulation colour initially. In addition for those formulations which exhibited an increase in colour when employing AACH with comparatively high water content, eg above 18% by weight, the invention water level selection in AACH avoids the region in which both colour change and efficacy impairment are increasing most rapidly with increase in water content.

Anhydrous herein with respect to the formulations indicates that the formulation is free or substantially free from unbound water, for example less than 1% by weight unbound water or preferably less than 0.5% or most preferably zero unbound water. It will be understood that the water which is present in the AACH constitutes bound water for the purposes of this specification.

According to a second aspect of the present invention there is provided a process for the preparation of an anhydrous antiperspirant or deodorant formulation comprising the step of suspending a particulate AACH in a water-immiscible carrier fluid, characterised in that the formulation is translucent and the AACH suspended in the carrier fluid has a water content in the range of from 9 to 18% by weight.

According to a third aspect of the present invention there is provided a cosmetic method for controlling or inhibiting perspiration or controlling the generation of body odours comprising the step of applying topically to a selected area of human skin an anhydrous antiperspirant or deodorant composition comprising particulate AACH, and a water-immiscible carrier fluid in which the AACH is suspended characterised in that the formulation is translucent and the AACH has a water content in the range of from 9 to 18% by weight.

DETAILED DESCRIPTION OF THE INVENTION

The present invention provides anhydrous, translucent, formulations containing a selected level of water specifically to ameliorate or eliminate the problem of formulation colour whilst maintaining high enhanced antiperspirant efficacy.

Activated Aluminium Chlorohydrate (AACH)

The level of water in the AACH employed herein is at least 9%, desirably at least 10% preferably at least 11% by weight, more preferably at least 12% by weight and especially at least 13% by weight. As the minimum lower limit for the level of water in the AACH increases, then so does the maximum colour of the formulation diminish. The level of water is not more than 18% particularly not more than 17%, especially not more than 16% by weight and in many embodiments not more than 15% by weight. By selecting the progressively lower upper limit for preferred levels of water in the AACH, then the minimum efficacy of the AACH is kept progressively higher. In some selected embodiments, the level of water in the AACH is about 14% by weight. In such a region, the colour of the formulation is at or near its minimum, whilst simultaneously the efficacy remains at or near its maximum.

AACH having the desired or preferred level of water content can be produced by employing known processes for making AACH, and preferably employing conditions during the reaction phase so as to maximise the production of Band III aluminium species, such as those described in U.S. Pat. No. 4,359,456 and controlling the conditions of the subsequent drying stage so as to retain the desired or preferred level of water content.

An alternative, and possibly more convenient method comprises the rehydration of a commercially available AACH having a water content of below 9 or 10% by weight, such as in the region of from 5 to 8% by weight. Suitable starting materials for rehydration include Aloxicol™ LR available from Giulini and A418™ from Summit. Rehydration can be effected by controlled exposure (time, temperature) to an atmosphere having a controlled relative humidity, for example an atmosphere in equilibrium with a saturated salt solution of specified salts. This is often more suitable for small scale production. An alternative comprising contacting the particulate AACH with water, desirably in droplet form with agitation to distribute the water substantially evenly through the mass of AACH. Suitable apparatus for combined spraying and agitation include gas-fluidised beds and mechanically agitating granulators, that either rotate or vibrate, and all equipped with a sprayer that can spray fluid onto the agitated particles. The rate of spraying and the extent of agitation is preferably controlled to control the extent to which the particle size distribution is altered during the rehydration, for example controlled to minimise any significant change in particle size distribution.

The yellowness of the AACH particles and on formulations containing them is suitably measured by determining its Δb value in accordance with the procedure and recommendations in ISO 105 J01 of 1982 (E). The measurements are suitably conducted using a Colour Eye 7000™ reflectometer (Macbeth Division of Kalmorgan Instruments Corporation), calibrated in accordance with their instructions for yellow, and with the following settings:—specular—included; UV—excluded below 420 nm. The reflectance values are converted into X, Y and Z tristimulus values using the colour matching functions in the CIE 1964 supplementary standard calorimetric system (10 degree observer data) for illuminant D56. The yellowness $\Delta b$ is calculated from the tristimulus values using the equations given in recommendation no 2 of supplement no 2 to CIE publication No 15, given the value of the reference tiles.

It is desirable to employ AACH which has a $\Delta b$ value, measured in accordance with the method described herein, of below 2, desirably below 1.5, preferably below 1.0 and especially below 0.5. Indeed, the $\Delta b$ value of the AACH can be employed as an alternative or additional parameter for selecting AACH for employment in anhydrous antiperspirant or deodorant formulations.

The efficacy of formulations containing AACH can be previewed by measuring its Band III content. A suitable method for use herein comprises Standard Basic Aluminium Chloride Solution Size Exclusion Chromatogram of the Size Exclusion Chromatography Test, as described in the above-mentioned U.S. Pat. No. 4,359,456, the relevant content of which is incorporated herein by reference.

It is desirable to select AACH having a Band III content, when measured by the method described herein, of greater than 30%, more desirably of greater than 35% and preferably greater than 40%. The Band III content can be employed as an alternative or additional parameter for selecting which AACH to employ in anhydrous formulations.

Hence, one convenient way to select AACH for incorporation in translucent anhydrous formulations or to judge whether a treatment to unsuitable AACH has rendered it suitable is to measure two of its parameters, namely its $\Delta b$ value and Band III content. Suitable AACH has a $\Delta b$ value of below 1.5 and a Band III content of above 30% and more suitable above 35%. Such a combination of parameters can be substituted for the water content parameter of the AACH to determine its suitability, or the selection can be based on all three parameters. AACH preferences can be made on the basis of combining the preferences for each of the three parameters. The particle size of the antiperspirant salts often falls within the range of 0.1 to 200 µm with a mean particle size often from 3 to 20 µm. Both larger and smaller mean particle sizes can also be contemplated such as from 20 to 50 µm or 0.1 to 3 µm.

It is highly desirable to employ AACH which not only has the desired water content, but which also has been milled. By so doing, it is possible to minimise or at least reduce by a significant extent the proportion of AACH particles which have substantial internal voids, ie are hollow. The elimination or removal of the hollow AACH particles tends to improve the potential transparency (light transmittance) of the anhydrous formulations by rendering it easier to achieve acceptable matching of the refractive indexes of the antiperspirant solids and the suspending water-immiscible fluid. Milling can be carried out using any suitable milling techniques can be employed, such as ball or swing milling.

The AACH particles often comprise from 1 to 35% by weight of the formulation, particularly from 5% an especially from 15% by weight. In many embodiments, the formulations contain from 20 to 30% AACH particles, for example from 23 to 26%. Herein, in relation to the formulation, all percentages are by weight based on the entire formulation, unless otherwise stated, and in respect of the AACH particles, their weight includes any water content.

When only a low concentration of AACH is present, it tends to provide deodorant properties, and when a high concentration of AACH is present, it provides antiperspirancy.

Suspending Carrier

The suspending carrier fluid can be any water-immiscible (hydrophobic) material that is liquid at ambient temperature or just below, for example at 15° C. It is normally present in the range of from 20 to 99% of the formulation, and in many embodiments from 30 to 75%. In some embodiments, it constitutes the balance of the formulation together solely with the AACH antiperspirant, and in other formulations an additional constituent or constituents can be present as well, including particularly a thickener or structurant and/or optional ingredients which will be described more fully subsequently herein.

The carrier liquid can be selected from both volatile and non-volatile liquids and mixtures which contain both a volatile and a non-volatile liquid. The relative proportions of the volatile and non-volatile liquids are at the discretion of the user and will usually be chosen in association with the other formulation constituents in order that the formulation exhibits the desired combination of properties.

It may have some volatility but its vapour pressure will generally be less than 4 kPa (30 mmHg) at 25° C. so that the material can be referred to as an oil or mixture of oils. More specifically, it is desirable in some embodiments, that at least 80% by weight of the hydrophobic carrier liquid should consist of materials having a vapour pressure not above 4 kPa at 25° C.

In some cosmetic formulations, the hydrophobic carrier liquid includes a volatile liquid silicone, i.e. liquid polyorganosiloxane, preferably not more than 50% of the liquid carrier and more preferably not more than 20%, in order to render easier the formation of a translucent formulation. To class as "volatile" such material should have a measurable vapour pressure at 25° C. Typically the vapour pressure of such a volatile silicone lies in a range from 1 or 10 Pa to 2 kPa at 25° C. It is desirable to include volatile silicone because it gives a "drier" feel to the applied film after the composition is applied to skin.

Volatile polyorganosiloxanes can be linear or cyclic or mixtures thereof. Preferred cyclic siloxanes include polydimethylsiloxanes and particularly those containing from 3 to 9 silicon atoms and preferably not more than 7 silicon atoms and most preferably 4, 5 and/or 6 silicon atoms, otherwise often referred to as cyclomethicones. Preferred linear siloxanes include polydimethylsiloxanes containing from 3 to 9 silicon atoms. The volatile siloxanes normally by themselves exhibit viscosities of below $10^{-5}$ m²/sec (10 centistokes), and particularly above $10^{-7}$ m²/sec (0.1 centistokes), the linear siloxanes normally exhibiting a viscosity of below $5 \times 10^{-6}$ m²/sec (5 centistokes). The volatile silicones can also comprise branched linear or cyclic siloxanes such as the aforementioned linear or cyclic siloxanes substituted by one or more pendant -0-Si(CH₃)₃ groups. Examples of commercially available silicone oils include oils having grade designations 344, 345, 244, 245 and 246 from Dow Corning Corporation; Silicone 7207 and Silicone 7158 from Union Carbide Corporation; and SF1202 from General Electric.

The hydrophobic water-immiscible liquid carrier employed in many compositions herein can alternatively or additionally comprise non-volatile silicone oils, which include polyalkyl siloxanes, polyalkylaryl siloxanes and polyethersiloxane copolymers. These can suitably be selected from dimethicone and dimethicone copolyols. Commercially available non-volatile silicone oils include Dow Corning 556 and Dow Corning 200 series. In some embodiments, such non-volatile oils provide from 1 to 30% of the liquid carrier and in others from 30 to 75%.

Some highly desirable non-volatile silicones comprise methylphenyl polysiloxanes. Desirably, the polysiloxane is short chain and linear, such as a disiloxane, trisiloxane or tetrasiloxane. Particularly desirably, the mole ratio of alkyl (especially methyl) to phenyl substitution is 1:1. It is especially desirable to select within the class of non-volatile polysiloxane materials those which have a viscosity of below 300 centistokes and advantageously those of below 200 centistokes. In practice, the viscosity of preferred siloxane materials is often in the region of 50 centistokes or higher. Examples of highly preferred non-volatile siloxanes include PDM-7040 and PDM-7050 (trade names) obtainable from Gelest and DC 704 (trade name) obtainable from Dow Corning Inc.

The water-immiscible liquid carrier may contain from 0 to 100% by weight of one or more liquid silicones. Various desirable embodiments herein contain silicone liquids in at least 10% by weight of the whole formulation. In many instances, when both a volatile and a non-volatile silicone oil is present, their respective weight ratios are chosen in the range of from 1:1 to 1:40. In other embodiments, liquid silicones are absent or present in only a small proportion of the liquid carrier, such as up to 7 or 8%.

Silicon-free hydrophobic liquids can be used instead of, or in addition to liquid silicones. Silicon-free hydrophobic organic liquids which can be employed include volatile or non-volatile liquid aliphatic hydrocarbons such as mineral oils or branched aliphatic hydrocarbons often selected to exhibit a low viscosity. Examples of liquid hydrocarbons are hydrogenated polyisobutene, polydecene, and paraffins and/or isoparaffins of at least 10 carbon atoms.

Other suitable constituents of hydrophobic carriers are liquid aliphatic or aromatic esters.

Suitable aliphatic esters contain at least one long chain alkyl group, such as esters derived from $C_1$ to $C_{20}$ alkanols esterified with a $C_8$ to $C_{22}$ alkanoic acid or $C_6$ to $C_{10}$ alkanedioic acid. The alkanol and acid moieties or mixtures thereof are preferably selected such that they each have a melting point of below 20° C. These esters include isopropyl myristate, lauryl myristate, isopropyl palmitate, diisopropyl sebacate and diisopropyl adipate. It can sometimes be desirable to restrict their presence to not more than about 20% by weight of the carrier liquid.

Suitable liquid aromatic esters, preferably having a melting point of below 20° C., include fatty alkyl benzoates alkylene dibenzoate, alkoxylated alkyl benzoate or a polyalkylene oxide dibenzoate, or a mixture of two or more. The alkyl group is linear or branched and often contains at least 8 carbons, in many instances up to 25 carbons, eg from C8 to C18 or is a mixture, eg C12–C15. The term alkylated herein includes alkylene groups which are terminated at each end with a benzoate group. The alkylene group often contains from 2 to 6 carbons and can be linear or branched, a suitable example of linear being propylene.

Further instances of suitable hydrophobic carriers comprise liquid aliphatic ethers derived from at least one fatty alcohol, such as myristyl ether derivatives e.g. PPG-3 myristyl ether or lower alkyl ethers of polyglycols such as butyl ether of PPG-14 to PPG-18. The ethers commonly contain between 20 and 65 carbons.

Yet other liquid carriers comprise branched aliphatic alcohols containing from 12 to 25 carbons, including isostearyl alcohol and octyldodecanol, although often at not more than about 20% of the carrier liquid.

It will be recognised that at least some of the liquid carriers can alternatively be viewed as emollient oils. As such they can be included in order to provide both carrier and emollient functions.

In the absence of a structurant or thickener, the formulation adopts typically the form of a lotion, often having a relatively low viscosity, though the latter depends on which carrier liquids are present. Such lotions are often suitable for dispensing in roll-on squeeze spray dispensers or for absorption into an absorbent structure, such as an absorbent sponge, pad or sheet or as a surface film on a non-absorbent sheet.

Formulation Appearance

The formulations in the first aspect herein are translucent on being dispensed from the dispenser, that is to say permit the transmission of at least 0.02% and preferably at least 0.04% of light at a wavelength of 580 nM through a thickness of 1 cm. Such an extent of light transmission is particularly suited to formulations when they are dispensed in the form of a narrow band or stream, such as a lotion or an anhydrous cream or soft solid. When the formulation is intended to be translucent not only within a typical dispensing package, but also in the fine stream that is dispensed through its dispensing orifice, it preferably has a light transmission of at least 1% through a thickness of 1 cm.

Structurant or Thickener

In many formulations herein, the carrier liquid is thickened to a higher viscosity or structured to transform the formulation to a soft solid which can flow under pressure or to a firm solid which retains its integrity under conventional use conditions. The thickener and/or structurant is normally employed in an amount selected to provide the desired extent of thickening or structuring, and takes into account the inherent capability of the thickener or structurant. As would be expected, variations in the proportions of carrier and a specified thickener/structurant alters the viscosity or hardness of the eventual product. Likewise, the various thickeners and structurants are not equally effective on a weight basis, so that for some, a higher concentration is needed to achieve a similar increase in viscosity or hardness than for others. Likewise, the various classes of liquid carrier are not equally susceptible to being thickened or structured by the chosen material.

Taking into account the foregoing, the amount of structurant or thickener or combination of thickeners and/or structurants is chosen in practice to achieve the desired product form and is usually selected within the range of from 0.2 to 35% by weight based on the formulation and in many instances from 5 to 25%. Expressed alternatively, the proportion of thickener or structurant is often from 1% to 80% of the liquid carrier, and in many instances from 10 to 45% thereof.

Suitable thickeners can be inorganic or organic polymers.

The inorganic materials are commonly finely particulate silica or silicates. These include fumed silica, eg those available from Degussa under their tradename Aerosil. The silicates include complex silicates such as clays, such as bentonite, hectorite or montmorillonite. The surface of the particulate clay can be treated with a hydrophobe so as to render it more compatible with the carrier liquid, as for example in Bentone™ 38. The inorganic thickeners are commonly not included at greater than about 5% and often from 0.3 to 3% by weight of the formulation.

Suitable organic thickeners are often carbohydrates or polysaccharides such as starch, or hydrolysed derivatives. An especially desirable class or derivatives comprises dextrins and particularly esterified dextrins.

Preferred in this category is a dextrin fatty acid ester having the formula:

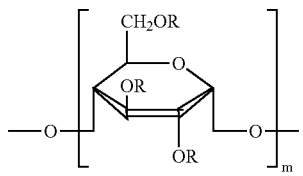

wherein each R group, individually, is a hydrogen atom or an acyl group having up to 22 carbon atoms, provided that at least one R group per glucose unit is an acyl group of at least 4 carbon atoms, and m has an average value from 5, 10 or 20 up to 50 or even up to 150, more preferably from 20 to 30. The dextrin fatty acid ester can be a partial ester, i.e. at least one R group is hydrogen; or the dextrin can be completely esterified, i.e., all R groups are acyl, such as a $C_4$–$C_{22}$ acyl group. The acyl groups may be the same or similar, and preferably they are straight chain acyl groups with chain lengths of 8 to 22 carbon atoms, e.g. in a range from 12 or 14 carbon atoms to 18 or 20 carbon atoms. Similar carbon number branched acyl groups may be employed.

An example of a suitable dextrin fatty acid ester is dextrin palmitate, available commercially as RHEOPEARL KL and RHEOPEARL FL, for example, from Chiba Flour Milling Co., Ltd. Other examples of esters of $C_8$–$C_{22}$ carboxylic acids are dextrin behenate, dextrin laurate, dextrin myristate, dextrin stearate, and mixtures thereof.

A further category of thickening polymer is block copolymers of styrene with ethylene propylene and/or butylene available from Shell under their trade name KRATON G, e.g. styrene ethylene/butylene styrene linear block copolymers available as KRATON G 1726X.

Yet other thickening polymers are co-polymers of alpha methylstyrene and styrene available from Hercules under the trade name KRISTALEX, e.g. KRISTALEX F85, with mean molecular weight of approximately 1200.

A still further class of thickening polymers comprises co-polymers of vinyl pyrrolidone with polyethylene containing at least 25 methylene units such as triacontanyl polyvinylpyrrolidone, available under the trade name Antaron WP-660.

Other suitable thickening polymers or structurants include polyamides as discussed in U.S. Pat. No. 5,500,209, including in particular terpolymers (e.g. Elvvamide 8061™) and polyamides based on complex fatty acids. Such polyamides may be derived from organic diamines containing 2 to 12, preferably 2 to 8 carbon atoms, condensed with di- or poly carboxylic acids containing 4 to 20 carbon atoms per carboxylic acid group (Versamid™ or Unirex™). Aromatic polyamide resins having pendant silyl groups are described in U.S. Pat. No. 5,243,010. The polyamides can be modified with silicon-containing moieties such as siloxanes containing lower alkyl or phenyl groups, as described for example in U.S. Pat. No. 5,874,069. Alternative polymers are described in U.S. Pat. No. 5,919,441 which are copolymers of organosiloxane diamines with dimeric acids. Related polymers described in U.S. Pat. No. 5,919,441 comprise polyurea in which organosiloxane diamines are reacted with a isocyanurate.

A still further class of polymer, which is more commonly regraded as a structurant rather than a thickener comprises siloxane elastomers, namely organic polysiloxanesαω which have been crossed linked, either lightly or extensively. Cross linking can arise in one way from reaction between Si—H groups and unsaturated groups, such as Si-vinyl groups or α, ω dienes, typically Pt catalysed. The elastomers are often blends containing absorbed volatile silicones. Examples include DC9010, DC9040 and DC9070 (Dow Corning Inc) KSG-17 (Shin-Etsu Chemical Co) SF 839 GE (General Electric) and Gransil SR-CYC (Grant Industries Inc). Various at least lightly cross-linked siloxane elastomers are described in U.S. Pat. No. 5,922,308.

Useful structurants are often selected from waxes, polymeric structurants and fibre-forming structurants.

This term "wax" is conventionally applied to a variety of materials and mixtures which have similar physical properties, namely that:-
  they are solid at 30° C. and preferably also at 40° C.;
  they melt to a mobile liquid at a temperature above 30° C. but generally below 95° C. and preferably in a temperature range of 40° C. to 90° C.;
  they are water-insoluble and remain water-immiscible when heated above their melting point.

Waxes herein are usually selected from hydrocarbons, silicone polymers, esters of fatty acids or mixtures containing such compounds along with a minority (less than 50%) of other compounds. Naturally occurring waxes are often mixtures of compounds which include a substantial proportion likely to be a majority of fatty esters. They form crystals in the water-immiscible liquid when it cools from the heated state during processing, commonly needles or platelets.

Examples of hydrocarbon waxes include paraffin wax, microcrystalline wax and polyethylenes with molecular weight of 2,000 to 10,000. Examples of ester waxes include esters of $C_{16}$–$C_{22}$ fatty acids with glycerol or ethylene glycol and these may be made synthetically. Examples of natural waxes include beeswax, carnauba and candelilla waxes which are of vegetable origin and mineral waxes from fossil remains other than petroleum. Montan wax, which is an example of mineral wax, includes non-glyceride esters of carboxylic acids, hydrocarbons and other constituents.

Further waxes employable herein comprise silicone polymer waxes, including waxes which satisfy the empirical formula:-

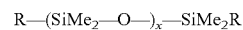

R—(SiMe$_2$—O—)$_x$—SiMe$_2$R in which x is at least 10, preferably 10 to 50 and R represents an alkyl group containing at least 20 carbons, preferably 25 to 40 carbons, and particularly having an average linear chain length of at least 30 carbons.

Other silicone waxes comprise copolymers of dimethicone and alkyloxymethicone, satisfying the general formula:-

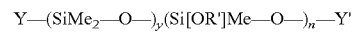

Y—(SiMe$_2$—O—)$_y$(Si[OR']Me—O—)$_n$—Y' in which Y represents SiMe$_2$—O, Y' SiMe$_2$, R' an alkyl of at least 15 carbons preferably 18 to 22 such as stearyl, y and z are both integers, totalling preferably from 10 to 50.

A second class of useful structurant is fibre-forming. Examples of this class are normally monomers or dimers having a molecular weight below 10,000 often below 2,000 which can gel hydrophobic organic liquids such as water-immiscible hydrocarbon and/or silicone oils. Gels made using them can be disrupted by shearing and lack the capability to recover their structure within a short time, unless remelted.

Materials with this ability to gel hydrophobic organic liquids with formation of a fibrous network have been reviewed by Terech and Weiss in "Low Molecular Mass Gelators of Organic Liquids and the Properties of their Gels" Chem. Rev 97, 3133–3159 [1997] and by Terech in Chapter 8, "Low-molecular weight Organogelators" of the book "Specialist surfactants" edited by I D Robb, Blackie Academic Professional, 1997.

When observed, the primary fibres in a such a gel are generally thin (diameter less than 0.5 μm, often less than 0.2 μm) and appear to have numerous branches or interconnections. Primary fibres may entwine to form a thicker strand.

One material which is well known to form such gels is 12-hydroxy stearic acid which is discussed in Terech et al "Organogels and Aerogels of Racemic and Chiral 12-hydroxy octadecanoic Acid", Langmuir Vol 10, 3406–3418, 1994. The material is commercially available from Ajinomoto and also from Caschem.

U.S. Pat. No. 5,750,096 is one of several documents which teaches that gelation can be brought about using esters or amides of 12-hydroxy stearic acid, the alcohol or the amine used in its preparation being an aliphatic (>2 carbons), cycloaliphatic (>4 carbons) or aromatic group (preferably fixed ring system) with up to 22 carbons therein. If the group is aliphatic it preferably contains at least three carbon atoms. s and may be a fixed ring system such as adamantyl. A specific example is lauric monoethanolamide also termed MEA lauramide.

N-acyl amino acid amides and esters are also known to structure liquids, as in U.S. Pat. No. 3,969,087. We have established that they do so by forming fibrous networks. N-Lauroyl-L-glutamic acid di-n-butylamide is commercially available from Ajinomoto under their designation GP-1. Further materials which have been disclosed as gelling agents are the amide derivatives of di and tribasic carboxylic acids set forth in WO 98/27954 notably alkyl N,N'dialkyl succinamides.

A structurant which is the subject of a co-pending application, published as WO 00/61096, is a combination of a sterol and a sterol ester.

In its preferred form the sterol satisfies either of the two formulae:

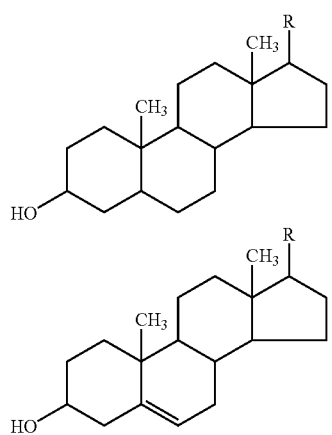

in which R represents an aliphatic, cycloaliphatic or aromatic group, and preferably a linear or branched aliphatic saturated or unsaturated hydrocarbon group. R desirably contains from 1 to 20 carbons and preferably from 4 to 14 carbons. It is particularly suitable to employ β-sitosterol.

The preferred sterol ester is oryzanol, sometimes referred to as γ-oryzanol which contains material satisfying the following formula:-

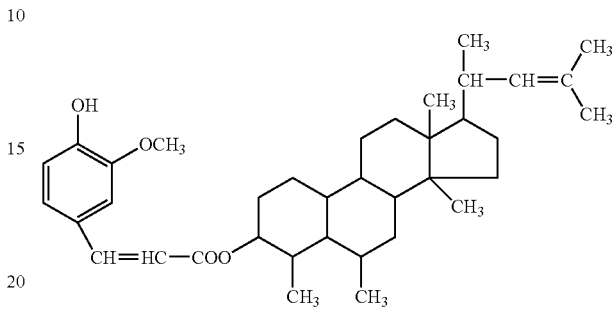

The sterol and sterol ester are used in a mole ratio that is normally selected in the range of from 10:1 to 1:10, especially from 6:1 to 1:4 and preferably in the range of from 3:1 to 1:2. Employment of the two system constituents within such a mole ratio range, facilitates the co-stacking of the constituents to form a fibrous network.

One further sterol which can be contemplated for structuring predominantly (>97% by weight) silicone oils comprises lanosterol, having the structure shown below and optionally containing a fraction of dihydrolanosterol.

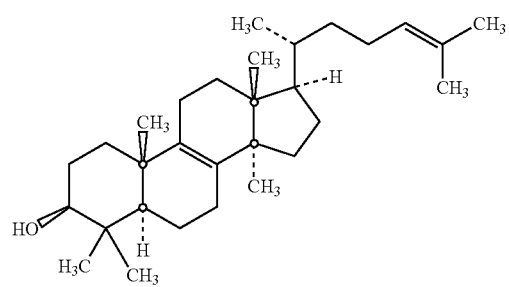

Another highly desirable structurant which is the subject of a co-pending application published as WO 00/61079 and which may be used in this invention is an ester of cellobiose and a fatty acid, preferably of 6 to 13 carbon atoms especially 8 to 10 carbon atoms. Preferably the cellobiose is fully esterified, or nearly so, and is in the α-anomeric form.

The structure of such a compound, in its α-anomeric form is:

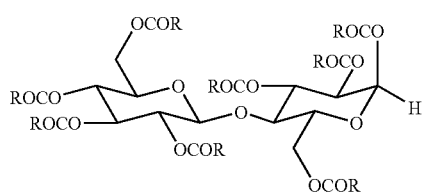

where R is an alkyl or alkenyl chain of 5 to 12 carbon atoms so that the acyl group contains 6 to 13 carbon atoms.

Particularly preferred acyl groups incorporate a linear alkyl chain of 7 to 9 carbon atoms and are thus octanoyl, nonanoyl or decanoyl.

The acyl groups may have a mixture of chain lengths but it is preferred that they are similar in size and structure, although at the anomeric carbon it is sometimes desirable to employ a dissimilar acyl group, which may an aliphatic group of different chainlength or an aromatic group. Thus, it is sometimes preferred that all of the acyl groups are aliphatic and at least 90% of the acyl groups have a chain length within a range such that the shorter and longer chain lengths in the range differ by no more than two carbon atoms, i.e. length in a range from m−1 to m+1 carbon atoms where m has a value in a range from 7 to 10.

Synthetic methods for the esterification of saccharides are well known. The esterification of cellobiose has been reported by Takada et al in *Liquid Crystals*, (1995) Volume 19, pages 441–448. This article gives a procedure for the production of the alpha anomers of cellobiose octa-alkanoates by esterification of β-cellobiose using an alkanoic acid together with trifluoracetic anhydride.

A further class of fibre-forming structurants which are described in a co-pending application, satisfy the general formula:-

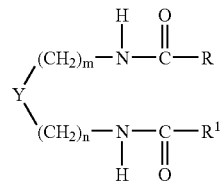

in which R and R' are each independently a linear or branched moiety containing 5 to 27 carbons, m and n are each independently 0 or 1, and Y is a cyclohexane ring bearing the two amido substituents shown above meta or preferably ortho to each other. Preferably R and R' are selected from C11 to C17. In the formula, m and n are preferably 1 when the amido substituents are meta to each other, and preferably 0 when the substituents are ortho to each other.

Optional Constituents

The formulations herein can additionally include a limited proportion of liquids at 20° C. which are not commonly seen as hydrophobic, especially if they are sufficiently compatible with the selected hydrophobic carrier liquids to form a single phase. An example of such additional liquids comprises a moisturiser such as glycerol, such as in a proportion of up to about 10% of the carrier liquid.

Optional ingredients in compositions of this invention can include deodorants, for example at a concentration of up to about 10% w/w to complement or supplement the AACH. Suitable deodorant actives can comprise deoperfumes, and/or microbicides, including particularly bactericides, such as chlorinated aromatics, including biguanide derivatives, of which materials known as Triclosan (Igasan DP300™), Tricloban™, and Chlorhexidine warrant specific mention. A yet another class comprises biguanide salts such as available under the trade mark Cosmosil™.

Other optional ingredients include wash-off agents, often present in an amount of up to 10% w/w to assist in the removal of the formulation from skin or clothing. Such wash-off agents are typically nonionic surfactants such as esters or ethers containing a $C_8$ to $C_{22}$ alkyl moiety and a hydrophilic moiety which can comprise a polyoxyalkylene group (POE or POP) and/or a polyol. The emulsifying surfactant can aid homogenisation of a polyol in the hydrophobic phase, spread of the formulation across the skin and subsequent wash-off. The intended purpose for the emulsifier will depend on the nature of the remaining constituents of the formulation and in particular on which liquid carriers are present and in what proportions.

The composition herein can incorporate one or more cosmetic adjuncts conventionally envisaged for antiperspirant soft solids. Such cosmetic adjuncts can include skin benefit agents such as allantoin or lipids, for example in an amount of up to 5%. Skin cooling agents such as menthol and menthol derivatives, often in an amount of up to 2%, all of these percentages being by weight of the composition. A commonly employed adjunct is a perfume, which is normally present at a concentration of from 0 to 4% and in many formulations from 0.25 to 2% by weight of the composition.

Dispensers

The compositions of the present invention are most conveniently dispensed from container types that are chosen in accordance with the rheology of the composition.

Compositions which have not been thickened or structured or which have been thickened to only a limited extent are best dispensed from roll-on or squeeze dispensers or pump sprays. Examples thereof are described in WO-A-00/643,202 and WO-A-00/44258. Designs of hand-operated squeeze sprays are shown in U.S. Pat. No. 4,122,979 and U.S. Pat. No. 4,278,206. The relevant invention formulations can be used in commercially available dispensers of those types.

In an additional aspect of the present invention, the apparent colour of formulations having a residual colour, can be reduced or eliminated as perceived by the human eye in or on the dispenser prior to application to the body, such as by employing packaging having a complementary colour in the face of the container wall in contact with the formulation. The complementary colour may be throughout the container wall or merely on its contact surface. This colour may be in the vicinity of the dispensing orifice in the package, such as the dispensing cover surrounding the dispensing orifice or orifices and/or particularly in the sidewall of the dispenser.

The use of a dispenser having a complementary colour is applicable to formulations obtained in accordance with other aspects of the present invention. However, the effect is visible in respect of both opaque and translucent formulations. It has been observed particularly with formulations that are translucent, such as for soft solids, creams, gels or lotions, either in the dispenser or when dispensed onto the surface of the pack, such as through a narrow slit, e.g. in the cover of the reservoir in the dispenser before application to the body. Soft solids are viewed after dispensing on to the surface or through the narrow dispensing slit or slits in the retaining cover on the dispenser reservoir. Solid sticks are conventionally dispensed through the top orifice of a cylinder and in this aspect are viewed through that orifice. A container wall may itself be translucent or opaque. The important feature of this aspect of the invention is that the contact surface of the wall is coloured with a complementary colour so that when the formulation is observed, it has a different appearance to the human eye, compared with when a white or non-complementary coloured contact wall surface is employed.

The colour and intensity of the colour of the formulation is measured in order to determine the appropriate complementary colour and intensity for the packaging, in accordance with known practice for colour measurements, to seek achromicity, taking into account the thickness of the formulation being stored or dispensed and the thickness of the container wall.

For convenience, the complementary colour can be obtained in the package by incorporating pigment or dye into the dispenser wall or cover material, usually a plastics material, preferably before the dispenser is moulded. Any relevant wall of the dispenser, such as side wall, can be translucent, to enable the composition to appear whiter to the human eye when it is stored in the dispenser. Alternatively, a coloured sleeve of that colour can be employed in conjunction with, wrapped around, a translucent wall of stick or soft solid dispenser, for example by shrink wrapping. The colour of the sleeve is transmitted through the translucent wall to the interior surface of the dispensing container.

In the instance of formulations having a yellowish colour, the complementary colour for the packaging material surface, ie that which on addition to the formulation colour can produce an achromic mixture, tends to be a dark green or similar colour. Likewise, if pale green or blue formulations were to be incorporated in packaging, the complementary colour would be yellow.

Compositions which have been thickened to form a cream or gelled to form a soft solid, ie materials which flow no more than slowly, except when subjected to hand-pressure, can be dispensed using a dispenser having a reservoir provided with a cover having at least one narrow dispensing aperture (slit). The relevant invention formulations can be employed in commercially available dispensers for soft solids or creams. Various examples of suitable dispensers are described in U.S. Pat. Nos. 6,039,483, 5,000,356, 4,865,231, 5,839,622 and 5,725,133.

Compositions which have been structured to form a firm solid can be dispensed using stick dispensers, including such dispensers which are commercially available for that purpose. Suitable examples of stick dispensers are described in WO 00/08970 or U.S. Pat. No. 5,275,496.

The formulations of the present invention are applied topically to the area of the body on which it is desired to control odour generation or sweating. Those areas include particularly the armpits and the feet, and alternatively or additionally, any other part of the body in which sweat can be trapped.

Having described the invention in general terms, specific embodiments thereof will be described in greater detail by way of example only.

EXAMPLES AND COMPARISONS

Preparation of Samples of AACH Having Specified Water Contents

The AACH employed in Comparison A was Aloxicol LR from Guilini having a water content of 5.5% by weight which had been milled to substantially remove voids within the particles (reference G0). The water content of further samples of G0 was modified by the method below:-

A saturated salt solution was placed at the bottom of a dessicator to control the humidity. Powder active G0 was then placed in a crystallising dish and placed in the dessicator. The powder was stirred intermittently to aid the uniform uptake of the water vapour. The amount of water absorbed by the active powder depended on the salt used (water activity, $a_w$) and the length of exposure time.

TABLE 1

| AACH reference | Saturated salt solution | $a_w$ | Exposure (hours) | % $H_2O$ |
|---|---|---|---|---|
| G1 | $Mg(NO_3)_2$ | 0.53 | 48 | 10.4 |
| G2 | KCl | 0.84 | 48 | 12.0 |
| G3 | $NaNO_3$ | 0.74 | 72 | 14.3 |
| G4 | KCl | 0.84 | 66 | 16.1 |
| G5 | $NaNO_3$ | 0.74 | 96 | 17.6 |
| G6 | KCl | 0.84 | 96 | 23.1 |

Water Content Measurement

Water content in the actives was measured using Sartorius™ Moisture Analyzer model MA30. A fixed weight of powder (2.0 g) was placed on an aluminium pan and then placed on the analyser balance. The powder was then heated at 100° C. via a heating element above the sample, until no further weight loss occurred, and reweighed.

Sample S0 was obtained from Summit under their grade designation A418 ready milled to substantially remove voids within the particles. The water content of further samples of S0 was modified using the same general method as described for modifying the water content of G0, resulting in material with the following characteristics:-

TABLE 2

| AACH reference | % $H_2O$ |
|---|---|
| S0 | 7.7 |
| S1 | 17.2 |
| S2 | 24.4 |

The yellowness of the each of samples G0 to G6 and S0 to S2 was measured using the reflectance method described below.

The Band III content of each sample of AACH was measured by the methods described hereinbelow.

Preparation of Formulations

In each of the Examples and Comparisons, the respective AACH sample was incorporated in the representative formulation below.
10% dextrin palmitate (Chiba)
25.5% AACH
64.5% C12-15 alkyl benzoate, Finsolv TN (Finetex)

The carrier, alkyl benzoate and thickener, dextrin palmitate were weighed into a glass beaker. The mixture was stirred gently and its temperature raised until all the structurants had dissolved. The mixture was then cooled to 80° C. and the AACH powder slowly added and thoroughly dispersed. Stirring was continued whilst the mixture was cooled to about 5–20° C. above its gelling/setting point (prior tested on a representative sample) whereupon it was poured into a 1 cm path length polymethyl methacrylate (PMMA) cuvette and allowed to cool and set.

The light transmission and the colour of the samples in the cuvettes was measured when they had cooled to ambient (about 22° C.) using the method described below.

The properties of the AACH samples and the formulations containing them are summarised in Tables 3 and 4 below. All the Examples and comparisons has a light transmission of greater than 0.04% in the 1 cm path length.

TABLE 3

| Example/Comparison AACH active | CA G0 | Ex1 G1 | Ex2 G2 | Ex3 G3 | Ex4 G4 | Ex5 G5 | CB G6 |
|---|---|---|---|---|---|---|---|
| % water content of active | 5.8 | 10.4 | 12.0 | 14.3 | 16.1 | 17.6 | 23.2 |
| % Band III by GPC | 49.8 | 49.4 | 49.0 | 47.0 | 47.0 | 40.8 | 20.3 |
| Yellowness (Δb) of active | 4.36 | 1.46 | 0.83 | 0.38 | 0.23 | 0.02 | −0.07 |
| Yellowness (Δb) of formulation | 2.51 | 0.69 | −0.07 | −0.36 | −0.97 | −0.31 | 0.79 |

TABLE 4

| Example / Comparison | CC | Ex6 | CD |
|---|---|---|---|
| AACH Active | S0 | S1 | S2 |
| % water content of active | 7.7 | 17.2 | 24.4 |
| % Band III by GPC | 46.2 | 35.5 | 11.7 |
| Yellowness (Δb) of active | 3.95 | −0.24 | −0.23 |
| Yellowness (Δb) of formulation | 1.62 | −0.61 | n/d |

(n/d indicates that the measurement was not made)

From Tables 3 and 4, it can be seen that the colour of the AACH particles and of the formulations made incorporating such AACH particles was unacceptably high in Comparison formulations CA, and CC. The Tables also show that the efficacy of the formulations was unacceptably low in Comparisons CB and CD, as demonstrated by the low Band III value in the AACH sample.

It can also be seen that the best combination of properties in the formulation occurs in the region of about 12 to 18% water content in the AACH.

Yellowness Measurement on Powder and Formulation

The measurement of yellow colour and colour differences, in particular the yellowness colour delta b (Δb) value for our materials was made following the recommendations given in ISO 105 J01 1982 (E).

Colour measurements were made using a Colour Eye 7000™ reflectometer manufactured by the Macbeth Division of Kolmorgan Instruments Corporation. The instrument was calibrated following the manufacturer's instructions and the measurements made using the following settings: specular included, UV excluded below 420 nm (by means of a Perspex filter) and a small sized aperture (0.75 cm×1.0 cm).

The samples, be they powdered AACH or formulations, were placed in cuvette cells (1 cm path length) made from poly(methylmethacrylate) and placed in front of the measuring port. Reflectance measurements were taken on all four sides of the cuvette and the average taken for the conversion.

The reflectance values obtained were then converted into X, Y and Z tristimulus values, using the colour matching functions in the CIE 1964 supplementary standard calorimetric system (10 degree observer data) for illuminant D65. A standard white tile supplied by the instrument manufacturer for calibration was used as the reference and measurements made under identical conditions and X, Y and Z tristimulus values also calculated.

Both sets of tristimulus values were then converted into L*,a* and b* colour space values using the equations given in Recommendation 2 of supplement No. 2 to CIE Publication No. 15. The white reference tile reference has the following values ($L^*_{ref}$=96.14, $a^*_{ref}$=−0.18, $b^*_{ref}$=1.03). Colour differences were then calculated by reference to these white tile values by the following equations.

$$\Delta L = L^* - L^*_{ref}$$

$$\Delta a = a^* - a^*_{ref}$$

$$\Delta b = b^* - b^*_{ref}$$

where the subscript ref refers to the appropriate values of the reference tile.

Δb is the yellowness value given in Tables 3 and 4 above.

Light Transmission

The translucency of a composition may be measured by placing a sample of standardised thickness in the light path of a spectrophotometer and measuring transmittance, as a percentage of light transmitted in the absence of the gel.

We have carried out this test using a dual-beam spectrophotometer. The sample of composition was poured hot into a 4.5 ml cuvette made of polymethylmethacrylate (PMMA) and allowed to cool to an ambient temperature of 20–25° C. Such a cuvette gives a 1 cm thickness of composition. Measurement was carried out at 580 nm, with an identical but empty cuvette in the reference beam of the spectrophotometer, after the sample in the cuvette had been held for 24 hours. We have observed that a composition which gives a transmittance of only 0.02% in this test is perceived by eye as "translucent" when extruded in a thickness less than 0.5 cm. A transmittance measured at any temperature in the range from 20–25° C. is usually adequately accurate, but measurement is made at 22° C. if more precision is required.

Measurement of Band III Content of AACH

The method employed was the Standard Basic Aluminium Chloride Solution Size Exclusion Chromatogram of the Size Exclusion Chromatography Test, as described in U.S. Pat. No. 4,359,456.

Characterisation of materials containing species differing in size by means of size exclusion chromatography (SEC) is generally known. The method of size exclusion chromatographic procedures used for the characterisation of AACH employed in this invention is as outlined below, and is used for characterisation on the basis of the percentage of aluminium in species less than 100 Angstroms in size.

The analytical procedure used to determine the percentage of aluminium in species having a size less than 100 Angstroms (i.e. material in Bands I, II, III, and IV) was performed using a stainless steel column of dimensions 30 cm long and 7.0 mm internal diameter. This was packed with spherical porous silica of nominal particle size 5 micrometers diameter, an average pore size of 50 Angstroms diameter, a pore volume of 0.8 cc/g and a surface area of 450 m²/g. A suitable silica was that available commercially as Nucleosil 50 from Macherey-Nagel GmbH.

Although the columns used in the actual method employed by the Applicants were obtained ready packed from Jones Chromatography Limited of Hengoed, Mid-Glamorgan, Wales, if it were necessary to pack a column with the silica it could conveniently be carried out by the high-pressure slurry method (see "Silica Gel and Bonded Phases, Their Production, Properties and Use in LC", by R P W Scott, Published by John Wiley and Sons, 1993, page 60) using hexane as the packing medium. In all cases the column would be equipped at the bottom with a zero dead volume fitting containing a 2 micrometer porosity stainless steel support and after packing would be capped with another zero dead volume fitting containing a 2 micrometer stainless steel frit.

The packed column was connected into a chromatographic system consisting of an automatic sampler, high-pressure pump, column, and a differential refractive index detector to monitor sample fractions as they were eluted. The refractive index detector was linked to an integrator to provide a real-time chromatogram and a data system that was programmed to calculate the relative chromatographic band areas of the fractions as a function of their elution times. The system was instructed to measure the areas of bands not resolved to the baseline by dropping perpendiculars from the lowest point of the valleys separating the bands to the baseline.

Newly packed columns were eluted with 200 ml of methanol at a flow rate of about 10 ml/minute, using a high pressure pump, to consolidate the bed and wash out the packing medium. This was followed by a change of eluent to the medium to be used for the analytical separations, in this case an aqueous solution containing 0.1 molar sodium nitrate and 0.01 molar nitric acid, and elution continued at a rate of 0.5 ml/minute until a flat base-line was achieved.

To provide a sample for conditioning the column and to act as a calibration standard a Standard Basic Aluminium Chloride Solution was prepared. This was carried out by dissolving 52.1 g of aluminium powder (99.97% aluminium by weight, grade 20/D supplied by The Aluminium Powder Company Limited of Holyhead, Anglesey, North Wales) in a solution of 93.2 g of aluminium chloride hexahydrate (supplied by Sigma-Aldrich Company Limited of Gillingham, Dorset SP8 4XT, UK) in 354.7 g of deionized water at about 90° C. in a stirred vessel equipped with a reflux condenser. When all of the aluminium had dissolved the solution was filtered to remove traces of insoluble impurities and allowed to cool to room temperature. This gave a Standard Basic Aluminium Chloride Solution that contained 12.5% aluminium by weight.

The column was conditioned by the application of multiple injections of 10 microlitre samples of the Standard Basic Aluminium Chloride Solution, diluted to 2.5% aluminium by weight, until a constant chromatogram was obtained from successive injections.

To prepare test solutions of materials for analysis for their Band I, II, III, and IV contents, those already in solution were used undiluted unless the aluminium concentration exceeded 2.5% by weight aluminium, in which case they were diluted with deionized water to provide a solution containing 2.5% by weight aluminium. Solid materials were dissolved in deionized water to give solutions containing 2.5% by weight aluminium. These solutions were treated in an ultrasonic bath for two minutes then filtered through 0.2 micrometer porosity cellulose acetate filter units. The preparation of the test solutions was carried out within 10 minutes of their application to the column. Sample solutions were applied to the top of the column as 1 microlitre injections and eluted at a rate of 0.5 ml/minute.

When a sample of Standard Basic Aluminium Chloride Solution was diluted to 2.5% aluminium by weight and applied to the column four main bands were obtained. They were characterised by means of the ratio of the retention times of the principal peak in each band to the retention time of the peak due to the totally included species (in the case of basic aluminium chlorides the totally included species arise from the presence of hydrochloric acid. This can be shown by comparison of its retention time with that of a sample of 0.01 molar hydrochloric acid.) and their chromatographic band areas expressed as percentages of the total chromatographic band area representing aluminium-containing material:

|  | Band I | Band II | Band III | Band IV |
|---|---|---|---|---|
| Relative retention time (minutes) | 0.66 | 0.75 | 0.81 | 0.94 |
| Band area (% of total aluminium band area) | 26.1 | 61.3 | 8.4 | 4.2 |

Comparison of the total aluminium content of the eluted fractions representing Bands I to IV with that of another sample of the same volume that had not passed through the column showed that there was complete elution of aluminium species from the column. In a further experiment it was found that the relative aluminium contents of the separated fractions, expressed as percentages of the total aluminium contents of Bands I to IV, agreed closely with the relative area percents determined by integration of the signals from the refractive index detector for the same bands.

It will be appreciated by those skilled in the art that mechanisms of separation other than the principal mechanism of size exclusion may play a part in this type of chromatography. Examples of the processes would be adsorption effects and hydrodynamic effects. Thus although it is possible for a given column and constant operating conditions to lead to invariable relative retention times, minor variations in particle size range and pore size distribution of the packing materials may lead to slight differences in relative retention times and the splitting of the main bands. In our experience with standard columns packed with different batches of the specified packing material, the four aluminium-containing bands consistently fall within the ranges indicated:

|  | Band I | Band II | Band III | Band IV |
|---|---|---|---|---|
| Relative retention time (minutes) | 0.56–0.72 | 0.73–0.79 | 0.80–0.87 | 0.88–0.98 |

Quantitatively, the amount of aluminium in the various Bands expressed as a percentage of the total aluminium of the compound under test is given by:

$$\% \text{ Aluminium in Band } III = A_{III}/(A_I + A_{II} + A_{III} + A_{IV})$$

in which $A_I$ represents the area corresponding to the Band I fraction and $A_{II}$, $A_{III}$, and $A_{IV}$ correspondingly for Band II, Band III and Band IV.

Example 7 and Comparison CE

In this Example, a composition prepared in accordance with Example 3 was filled into a conventional dispenser for a soft solid, as described in relation to FIGS. 9 and 10 of U.S. Pat. No. 6,039,483 (Plastek) having a rotating inner housing that acts as a reservoir for the composition and an outer housing which acts as a support for the inner housing, a cover for the inner housing and rotary means to elevate a platform within the inner housing. The cover was white opaque plastic and perforated by a design of eight radial gently arcuate slits of 4 mm width and 12 mm length. In Example 7, the inner housing that is in contact with the composition had an opaque dark green plastic sidewall. In addition, the sidewall of the outer housing was also of the same colour. In comparison CE, a further sample of the same composition was filled into a similar dispenser in which the interior and outer housings were made from opaque white plastic, but was otherwise the same as the green dispenser of Example 7.

A panel of persons skilled in the preparation of soft solid antiperspirant compositions assessed, by eye, the apparent colour of the composition stored in each dispenser under sunny daylight conditions prevailing in the Wirral and also under laboratory ceiling fluorescent lights.

The panel assessed that the apparent colour of the composition in the green dispenser was less noticably yellow (and hence a more neutral colour) and more pleasing than that in the comparison white dispenser.

A similar difference is observable when substituting the compositions CA, CB, CC or CD or the other Example compositions for the Ex3 composition.

The invention claimed is:

1. An anhydrous antiperspirant or deodorant composition comprising particulate activated aluminium chlorohydrate (AACH), and a water-immiscible carrier fluid in which the AACH is suspended wherein the formulation is translucent and the AACH has a water content in the range of from 9 to 18% by weight.

2. A composition according to claim 1 wherein the AACH has a water content of at least 10%.

3. A composition according to claim 1 wherein the AACH has a water content of not more than 17% by weight.

4. A composition according to claim 1 wherein the AACH has a Δb value of below 1.5.

5. A composition according to claim 4 wherein the AACH has a Δb value of below 1.0.

6. A composition according to claim 4 wherein the AACH has a Δb value of below 0.5.

7. A composition according to claim 1 wherein the AACH has a Band III content of greater than 30%.

8. A composition according to claim 6 wherein the AACH has a Band III content of greater than 40%.

9. A composition according to claim 1 wherein the AACH employed therein has been made by halting the drying of an aqueous solution thereof at its selected water content.

10. A composition according to claim 1 wherein the AACH employed therein has been made by increasing the water content of an AACH feedstock having a water content of below 10% by weight.

11. An anhydrous antiperspirant or deodorant composition comprising particulate AACH, and a water-immiscible carrier fluid in which the AACH is suspended wherein the formulation is translucent and the AACH has a Δb value of below 2 and a Band III content of greater than 40%.

12. A composition according to claim 1 wherein the AACH employed therein has been milled.

13. A composition according to claim 1 wherein the composition contains from 1 to 35% by weight of the AACH.

14. A composition according to claim 1 wherein the carrier liquid comprises one or more hydrophobic liquids selected from the group consisting of non-volatile and/or volatile silicones, liquid aliphatic hydrocarbons and/or liquid aliphatic esters, liquid aromatic esters, liquid branched aliphatic alcohols and liquid aliphatic ethers of a fatty alcohol or a polyglycol.

15. A composition according to claim 14 wherein the carrier liquid further comprises one or more non-volatile liquids selected from non-volatile silicone oils and non-volatile aromatic esters.

16. A composition according to claim 14 wherein the proportion of carrier liquid is from 20 to 99% by weight.

17. A composition according to claim 1 wherein the composition contains additionally a thickener and/or structurant.

18. A composition according to claim 17 wherein the thickener or structurant is present in a proportion selected in the range of from 0.2 to 35% by weight.

19. A composition according to claim 18 wherein the thickener or structurant is present in an amount of from 10 to 45% by weight of the liquid carrier.

20. A composition according to claim 17 wherein the thickener is a polysaccharide or hydrolysate thereof.

21. A composition according to claim 20 wherein the thickener is a dextrin ester.

22. A composition according to claim 17 wherein the structurant is selected from the group consisting of waxes, fibre-forming structurants and polymeric structurants.

23. A composition according to claim 17 wherein the formulation is in the form of a soft solid.

24. A composition according to claim 23 wherein the formulation is opaque in bulk and translucent after being dispensed through a narrow slit.

25. An antiperspirant or deodorant product comprising a dispenser containing a composition according to claim 1.

26. A product according to claim 25 characterized in that the dispenser has a wall in contact with the composition stored therein having a colour complementary to that of the composition.

27. A product according to claim 26 wherein the composition is a soft solid, cream, gel or lotion.

28. A product according to claim 26 in which the composition has a yellow colour and the dispenser wall is green.

29. A composition according to claim 1 wherein the AACH has a water content of at least 12% by weight.

30. A composition according to claim 1 wherein the composition contains from 20 to 30% by weight AACH.

31. A composition according to claim 1 wherein the proportion of carrier liquid is from 30 to 80% by weight.

32. A composition according to claim 17 wherein the thickener or structurant is present in a proportion of 5 to 25%.

* * * * *